(12) United States Patent
McMurtray et al.

(10) Patent No.: US 11,382,875 B2
(45) Date of Patent: Jul. 12, 2022

(54) METHODS AND COMPOSITIONS FOR MODULATING β-AMYLOID/α7-NACHR INTERACTIONS

(71) Applicants: Lundquist Institute for Biomedical Innovation at Harbor-UCLA Medical Center, Torrance, CA (US); Collaborations Pharmaceuticals, Inc., Raleigh, NC (US)

(72) Inventors: Aaron McMurtray, Torrance, CA (US); Julia Chung, Torrance, CA (US); Natalie Diaz, Torrance, CA (US); Sean Ekins, Raleigh, NC (US)

(73) Assignees: Lundquist Institute for Biomedical Innovation at Harbor-UCLA Medical Center, Torrance, CA (US); Collaborations Pharmaceuticals, Inc., Raleigh, NC (US)

( * ) Notice: Subject to any disclaimer, the term of this patent is extended or adjusted under 35 U.S.C. 154(b) by 64 days.

(21) Appl. No.: 16/498,898

(22) PCT Filed: Apr. 5, 2018

(86) PCT No.: PCT/US2018/026308
§ 371 (c)(1),
(2) Date: Sep. 27, 2019

(87) PCT Pub. No.: WO2018/187606
PCT Pub. Date: Oct. 11, 2018

(65) Prior Publication Data
US 2021/0093587 A1 Apr. 1, 2021

Related U.S. Application Data

(60) Provisional application No. 62/482,867, filed on Apr. 7, 2017.

(51) Int. Cl.
*A61K 31/138* (2006.01)
*A61P 25/28* (2006.01)
*A61P 25/16* (2006.01)
*A61K 45/06* (2006.01)

(52) U.S. Cl.
CPC .......... *A61K 31/138* (2013.01); *A61K 45/06* (2013.01); *A61P 25/16* (2018.01); *A61P 25/28* (2018.01)

(58) Field of Classification Search
CPC .................................................. A61K 31/138
See application file for complete search history.

(56) References Cited

U.S. PATENT DOCUMENTS

| 3,337,628 A | 8/1967 | Crowther et al. |
| 2014/0010897 A1 | 1/2014 | Sams et al. |
| 2016/0107990 A1* | 4/2016 | Sinha ............... A61P 19/02 514/423 |

OTHER PUBLICATIONS

Dobarro et al. (2013) Int'l Journal of Neuropsycopharmacology, 16, 2245-2257.*
Dobarro et al., Propranolol reduces cognitive deficits, amyloid and tau pathology in Alzheimer's transgenic mice, International Journal of Neurosychopharmacology, 2013, vol. 16, No. 10, p. 2245-2257.
Kinne et al., Regioselective preparation of 5-hydroxypropranolol and 4'-hydroxy-diclofenac with a fungal peroxygenase, Bioorganic & Medicinal Chemistry Letters, 2009, vol. 19, No. 11, p. 2085-3087.

* cited by examiner

*Primary Examiner* — Paul V Ward
(74) *Attorney, Agent, or Firm* — Bret E. Field; Bozicevic, Field & Francis LLP

(57) ABSTRACT

Methods of modulating the interaction between β-amyloid and α7-nAChR are provided. Aspects of the methods include administering to the subject an effective amount of a naphthalene derivative active agent. Compositions and kits for practicing the subject methods are also provided. The methods, compositions and kits find use in treating a variety of applications, such as treating a subject for a neurodegenerative disease, e.g., Alzheimer's disease.

7 Claims, 4 Drawing Sheets

*Data points in boxes were omitted from calculations

METHODS AND COMPOSITIONS FOR MODULATING β-AMYLOID/α7-NACHR INTERACTIONS

CROSS-REFERENCE TO RELATED APPLICATION

This application is a national phase application of PCT Application No. PCT/US2018/026308 filed Apr. 5, 2018, which application, pursuant to 35 U.S.C. § 119 (e), claims priority to the filing date of the U.S. Provisional Patent Application Ser. No. 62/482,867, filed Apr. 7, 2017; the disclosures of which applications are herein incorporated by reference.

INTRODUCTION

Alzheimer's Disease (AD) is the most common type of dementia and the 6th leading cause of death in USA, affecting over 5.1 million adults over the age of 65 years in this country, and costing the economy over $150 billion per year. AD is a disorder directly impacted by the alpha-7-nicotinic acetylcholine receptor (α-7nAChR) and positive allosteric modulator (PAM) agonists represent a disease modifying class of compounds that have already been clinically validated. While the mechanisms underlying the AD pathophysiology are still partially unclear, aggregation of tau and β-amyloid proteins and decreased acetylcholine are a focus of many studies. To date animal studies of α-7nAChR PAMs performed in in vivo models of AD and have shown improvement in cognition as well as reduction in brain tau and β-amyloid pathology. Unfortunately, the therapies currently on the market for treatment of AD, namely four cholinesterase inhibitors and one NMDA inhibitor, are only symptomatic and do not affect the underlying disease mechanisms or alter the disease course. Consequently, new medications with disease modifying effects are desperately needed for this disorder.

Galantamine is a cholinesterase inhibitor used in the treatment of AD that was later found to have a dual action at the neuronal nicotinic acetylcholine receptor (nAChRs). nAChRs play key roles in modulating neurotransmission, cognition, anxiety, and sensory gating. Previous studies have also demonstrated that α7-nAChR in particular may play a central role in the pathophysiology of AD. The α7-nAChRs are ligand gated ion channels comprised of five alphα7 subunits and function in the regulation of intracellular calcium. By modulating intracellular calcium levels in discrete neuronal locations they influence numerous physiological processes in the central nervous system. These receptors are responsible for regulating pre- and post-synaptic neurotransmitter release, regulation of neuronal growth, and regulation of neuronal differentiation. Additionally, these receptors serve as a feedback mechanism modulating glutamatergic pathways. Because α7-nAChR agonists typically result in tolerance, an alternative approach is to use positive allosteric modulators (PAMs). Galantamine is also a α7-nAChR PAM and has been shown to slow cognitive and global decline in patients with AD as well as reduce behavioral symptoms in these patients. However, these effects are not disease modifying and it is not clear that Galantamine is able to function as an α7-nAChR PAM in people due to preferential functioning through its other mechanism of action as an acetylcholinesterase inhibitor.

PAMs (for which 2 potential types have been proposed) represent a new and potentially disease modifying class of compounds that are strongly supported by evidence from both in vitro and in vivo studies. Previous studies demonstrate the ability of α7-nAChR PAM compounds to affect both β-amyloid and tau deposition in AD. In AD, β-amyloid has been shown to bind with high affinity to neuronal α7-nAChR and this interaction is theorized to be important in the formation of amyloid plaques. Additionally, when the α7-nAChR is bound by β-amyloid it loses its normal functioning and activity, and causes rapid phosphorylation of tau which leads to abnormal accumulation and aggregation, followed by formation of the characteristic neurofibrillary tangles found in this disorder. When the α7-nAChR subunit is deleted in the mouse model of AD there is protection of synaptic integrity and relative preservation of learning and memory functions. It has therefore been suggested that disrupting the interaction between β-amyloid and the α7-nAChR is a possible therapeutic target for treating AD.

The α7-nAChR agonists comprise one class of compounds that are known to be able to disrupt this interaction between β-amyloid and α7-nAChR. Consequently, developing novel agonists that act through this mechanism and are well tolerated is an active area of research for developing potential new therapeutic agents in AD. Animal models serve as good predictors of the effect of α7 nAChR PAMs. For example galantamine slowed down plaque formation and behavioral decline in the 5XFAD mouse model of AD. This animal overexpresses amyloid precursor protein (APP) with three familial AD (FAD) mutations and the model recapitulates certain AD features such as memory impairment, plaque formation, reduced anxiety, and neuron loss.

SUMMARY

Methods of modulating the interaction between β-amyloid and α7-nAChR are provided. Aspects of the methods include administering to the subject an effective amount of a naphthalene derivative active agent. Compositions and kits for practicing the subject methods are also provided. The methods, compositions and kits find use in treating a variety of applications, such as treating a subject for a neurodegenerative disease, e.g., Alzheimer's disease.

DEFINITIONS

Figure 1:
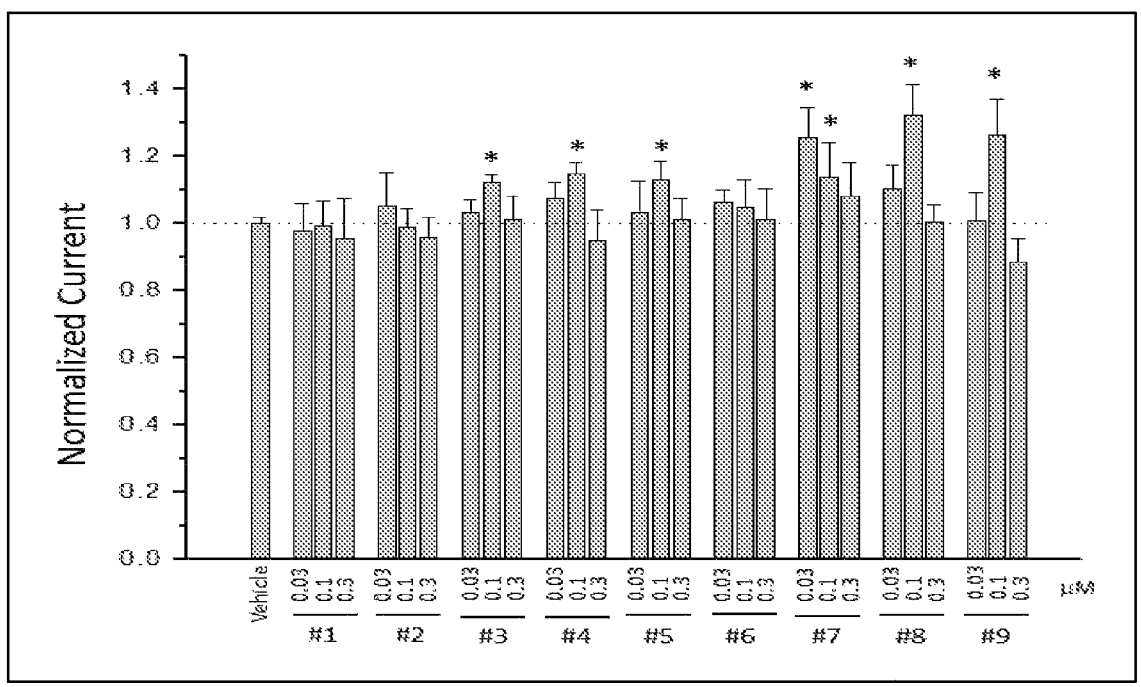
FIG. 1: α7-nAChR patch-clamp results for FDA approved compounds and Galantamine Derivatives.

Before describing exemplary embodiments in greater detail, the following definitions are set forth to illustrate and define the meaning and scope of the terms used in the description. Any undefined terms have their art recognized meanings.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). In some cases, alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. In some cases, alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein. The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Amino" refers to the group —NH$_2$. The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

Examples of heterocycles and heteroaryls include, but are not limited to, azetidine, pyrrole, imidazole, pyrazole, pyridine, pyrazine, pyrmidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

In addition to the groups disclosed with respect to the individual terms herein, substituent groups for substituting for one or more hydrogens (any two hydrogens on a single carbon can be replaced with $=O$, $=NR^{70}$, $-N-OR^{70}$, $=N_2$ or $=S$) on saturated carbon atoms in the specified group or radical are, unless otherwise specified, $-R^{60}$, halo, $=O$, $-OR^{70}$, $-SR^{70}$, $-NR^{80}R^{80}$, trihalomethyl, $-CN$, $-OCN$, $-SCN$, $-NO$, $-NO_2$, $=N_2$, $-N_3$, $-SO_2R^{70}$, $-SO_2O^-M^+$, $-SO_2OR^{70}$, $-OSO_2R^{70}$, $-OSO_2O^-M^+$, $-OSO_2OR^{70}$, $-P(O)(O^-)_2(M^+)_2$, $-P(O)(OR^{70})O^-M^+$, $-P(O)(OR^{70})_2$, $-C(O)R^{70}$, $-C(S)R^{70}$, $-C(NR^{70})R$, $-C(O)O^-M^+$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O) O^-M^+$, $-OC(O)OR^{70}$, $-OC(S)OR^{70}$, $-NR^{70}C(O)R^{70}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, $-NR^{80}R^{80}$ is meant to include $-NH_2$, $-NH$-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified: $-R^{60}$, halo, $-O^-M^+$, $-OR^{70}$, $-SR^{70}$, $-S^-M^+$, $-NR^{80}R^{80}$, trihalomethyl, $-CF_3$, $-CN$, $-OCN$, $-SCN$, $-NO$, $-NO_2$, $-N_3$, $-SO_2R^{70}$, $-SO_3^-M^+$, $-SO_3R^{70}$, $-OSO_2R^{70}$, $-OSO_3^-M^+$, $-OSO_3R^{70}$, $-PO_3^{-2}(M^+)_2$, $-P(O)(OR^{70})O^-M^+$, $-P(O)(OR^{70})_2$, $-C(O)R^{70}$, $-C(S)R^{70}$, $-C(NR^{70})R^{70}$, $-CO_2^-M^+$, $-CO_2R^{70}$, $-C(S)OR^{70}$, $-C(O)NR^{80}R^{88}$, $-C(NR^{70})NR^{80}R^{80}$, $-OC(O)R^{70}$, $-OC(S)R^{70}$, $-OCO_2^-M^+$, $-OCO_2R^{70}$, $-OC(S)OR^{70}$, $-NR^{70}C(O)R^{80}$, $-NR^{70}C(S)R^{70}$, $-NR^{70}CO_2^-M^+$, $-NR^{70}CO_2R^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not $-O^-M^+$, $-OR^{70}$, $-SR^{70}$, or $-S^-M^+$.

In addition to the groups disclosed with respect to the individual terms herein, substituent groups for hydrogens on nitrogen atoms in "substituted" heteroalkyl and cycloheteroalkyl groups are, unless otherwise specified, $-R^{60}$, $-O^-M^+$, $-OR^{70}$, $-SR^{70}$, $-S^-M^+$, $-NR^{80}R^{80}$, trihalomethyl, $-CF_3$, $-CN$, $-NO$, $-NO_2$, $-S(O)_2R^{70}$, $-S(O)_2O^-M^+$, $-S(O)_2OR^{70}$, $-OS(O)_2R^{70}$, $-OS(O)_2O^-M^+$, $-OS(O)_2OR^{70}$, $-P(O)(O^-)_2(M^+)_2$, $-P(O)(OR^{70})O^-M^+$, $-P(O)(OR^{70})(OR^{70})$, $-C(O)R^{70}$, $-C(S)R^{70}$, $-C(NR^{70})R^{70}$, $-C(O)OR^{70}$, $-C(S)OR^{70}$, $-C(O)NR^{80}R^{80}$, $-C(NR^{70})NR^{80}R^{80}$, $-OC(O)R^{70}$, $-OC(S)R^{70}$, $-OC(O)OR^{70}$, $-OC(S)OR^{70}$, $-NR^{70}C(O)R^{70}$, $-NR^{70}C(S)R^{70}$, $-NR^{70}C(O)OR^{70}$, $-NR^{70}C(S)OR^{70}$, $-NR^{70}C(O)NR^{80}R^{80}$, $-NR^{70}C(NR^{70})R^{70}$ and $-NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

"Pharmaceutically effective amount" and "therapeutically effective amount" refer to an amount of a compound sufficient to elicit the desired therapeutic effect (e.g., treatment of a specified disorder or disease or one or more of its symptoms and/or prevention of the occurrence of the disease or disorder). In reference to polyglutamine diseases, a pharmaceutically or therapeutically effective amount includes an amount sufficient to, among other things, prevent or cause a reduction of proteinaceous deposits in the brain of a subject.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N—C(H)—NH— ring atom arrangement, such as pyrazoles, imidazoles, benzimidazoles, triazoles, and tetrazoles. A person of ordinary skill in the art would recognize that other tautomeric ring atom arrangements are possible.

Also of interest as active agents for use in embodiments of the methods are prodrugs. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

The term "sample" as used herein relates to a material or mixture of materials, typically, although not necessarily, in fluid, i.e., aqueous, form, containing one or more components of interest. Samples may be derived from a variety of sources such as from food stuffs, environmental materials, a biological sample or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). In certain embodiments of the method, the sample includes a cell. In some instances of the method, the cell is in vitro. In some instances of the method, the cell is in vivo.

Other definitions of terms may appear throughout the specification.

DETAILED DESCRIPTION

Methods of modulating the interaction between β-amyloid and α7-nAChR are provided. Aspects of the methods include administering to the subject an effective amount of a naphthalene derivative active agent. Compositions and kits for practicing the subject methods are also provided. The methods, compositions and kits find use in treating a variety of applications, such as treating a subject for a neurodegenerative disease, e.g., Alzheimer's disease.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the present disclosure include methods of modulating the interaction, e.g., binding, between β-amyloid and α7-nAChR. In some instances, the methods are methods of at least reducing the binding of β-amyloid to α7-nAChR. By "at least reducing" is meant diminishing the magnitude or amount of binding by 2-fold or more, such as 5-fold or more, including 10-fold or more, of β-amyloid to α7-nAChR, as compared to a suitable control. In some instances, the methods result in substantially if not completely inhibiting binding of β-amyloid to α7-nAChR.

In practicing methods according to certain embodiments, a naphthalene derivative compound, e.g., propranolol or a novel derivative thereof (such as further described below), is contacted with a cell in which modulation of the interaction, e.g., binding, between β-amyloid and α7-nAChR is desired. Contact may be in vitro or in vivo, as desired. Where contact is in vivo, the methods may include administering an effective amount of a naphthalene derivative compound, e.g., propranolol or a novel derivative thereof (such as further described below), to an organism or subject in which modulation of the interaction, e.g., binding, between β-amyloid and α7-nAChR is desired.

In some instances, the methods are methods of treating a subject for a neurodegenerative, where the methods include administering to the subject an effective amount of naphthalene derivative compound (e.g., as described herein). In certain embodiments, the methods include: administering to a subject in need thereof an effective amount of a naphthalene derivative compound to treat the subject for the neurodegenerative disease. The term "treating" or "treatment" as used herein means the treating or treatment of a disease or medical condition in a patient, such as a mammal (such as a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of a subject compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of a subject compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

In some embodiments, the methods include co-administering the naphthalene derivative compound with a second active agent having therapeutic activity with respect to the target neurodegenerative disease. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some aspects of the subject methods, the method further comprises the step of measuring treatment efficacy. In some such instances, the determination is made by comparing the results to the results performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a neurodegenerative disease, e.g., using the methods described herein or known in the art. In some embodiments, the subject methods further comprise diagnosing an individual as having a neurodegenerative disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multisystem atrophy, glaucoma, ataxias, myotonic dystrophy, dementia, and the like. In some embodiments, the subject methods further comprise diagnosing an individual as having a disorder such as schizophrenia, traumatic brain injury, stroke, sepsis, myocardial infarction, cancer (non-small cell lung, breast, pancreatic), autism, chronic neuropathic pain, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

The above methods find use in a variety of different applications. Certain applications are reviewed in greater detail in the Utility section, below.

Naphthalene Derivative Compounds

Aspects of the present disclosure include naphthalene derivative compounds which find use in the methods of the invention, e.g., as described above, including treating a subject for a neurodegenerative disease. Naphthalene derivative compounds that may be employed in methods of the invention include, but are not limited to, those described in U.S. Pat. No. 3,337,628; the disclosure of which is herein incorporated by reference. In some instances, the naphthalene derivative has the structure of formula (I):

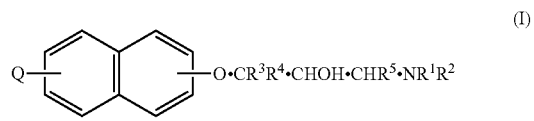

wherein:

$R^1$ is H or alkyl, cycloalkyl, alkenyl, aralkyl or alkanoyl radical, any of which may optionally be substituted;

$R^2$ is H or alkyl, cycloalkyl, alkenyl, alkynyl, or aralalkyl radical, any of which may optionally be substituted;

wherein R1 and R2 may joined together with the nitrogen atom to form a heterocyclic radical, which may optionally be substituted;

$R^3$, $R^4$, and $R^5$ are independently H or alkyl, which may optionally be substituted; and Q is optional and, if present, may be halogen, alkyl, substituted alkyl, hydroxy, alkoxy, substituted alkoxy, cyano, nitro, carboxy, carboxyamide, substituted carboxyamide, —$SO_3H$, sulfonamide, substituted sulfonamide, aryl, substituted aryl, heteroaryl, substituted heteroaryl, heterocycle and substituted heterocycle.

In some instances, the naphthalene derivative is propranolol, having the structure:

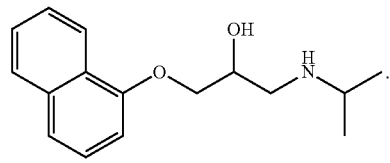 [SMILES: CC(C)NCC(O)COc1cccc2ccccc12]

In some instances, the naphthalene derivative is a compound having the structure of formula (II):

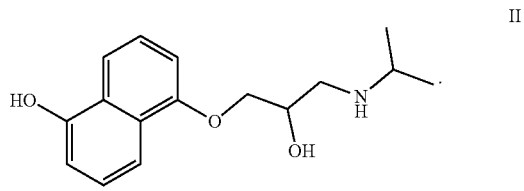 [SMILES: CC(C)NCC(O)COc1cccc2c(O)cccc12]

In some instances, the naphthalene derivative is a compound having the structure of formula (III):

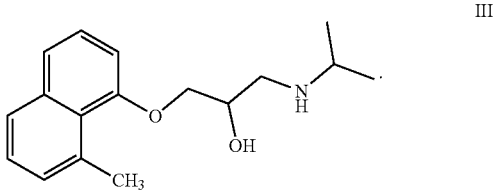 [SMILES: Cc1cccc2cccc(OCC(O)CNC(C)C)c12]

In some instances, the naphthalene derivative is a compound having the structure of formula (IV):

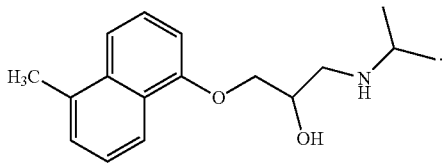

IV

In some instances, the naphthalene derivative is a compound having the structure of formula (V):

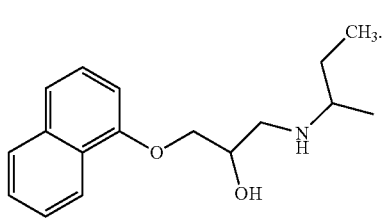

V

Aspects of the present disclosure include naphthalene derivative compounds (e.g., as described herein), salts thereof (e.g., pharmaceutically acceptable salts), and/or solvate, hydrate and/or prodrug forms thereof. In addition, it is understood that, in any compound described herein having one or more chiral centers (e.g., the 1-amino carbon center), if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Also provided are pharmaceutical preparations. Pharmaceutical preparations are compositions that include a naphthalene derivative compound (e.g., as described herein) (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Where the active agent is propranolol or a derivative thereof, e.g., as described above, the pharmaceutical formulation is a formulation as described in U.S. Pat. Nos. 4,201,866; 4,284,648; 4,428,926; 4,460,562; 4,522,804; 4,556,678; 4,600,708; 5,095,151; 5,116,867; 5,478,573; 5,776,985; 5,919,828; 6,500,454; 8,367,111; 9,040,086; and 9,358,214; the disclosures of which are herein incorporated by reference.

Utility

The subject methods find use in treating, including preventing, neurodegenerative diseases and/or aging-associated impairments and conditions associated therewith, such as impairments in the cognitive ability of individuals. Examples of neurodegenerative diseases and/or aging-associated impairments and conditions include the following:

Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's disease (AD). Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation. In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease. Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and asponteneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic lateral sclerosis. Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia. Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-system atrophy. Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods find use in treating individual as having a disorder such as schizophrenia, traumatic brain injury, stroke, sepsis, myocardial infarction, cancer (non-small cell lung, breast, pancreatic), autism, chronic neuropathic pain, and the like.

In some embodiments, the subject methods and compositions find use in slowing the progression of the target condition. In some instances, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

Combination Therapies

The subject compounds can be administered to a subject alone or in combination with an additional, i.e., second, active agent, as indicated above. As such, in some cases, the subject method further comprises administering to the subject at least one additional compound. Any convenient agents may be utilized, including compounds useful for treating viral infections. The terms "agent," "compound," and "drug" are used interchangeably herein. For example, naphthalene derivative compounds can be administered alone or in conjunction with one or more other drugs, such as drugs employed in the treatment of neurodegenerative disease conditions. In some embodiments, the method further includes coadministering concomitantly or in sequence a second agent. Second agents of interest include, but are not limited to, cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug with a pharmaceutical composition of the present disclosure means administration of the compound and second agent at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs and compounds of the present disclosure.

In some embodiments, the compounds (e.g., a subject compound and the at least one additional compound) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compounds and the second active agent. In pharmaceutical dosage forms, the compounds may be administered in the form of their pharmaceutically acceptable salts, or they may also be used alone or in appropriate association, as well as in combination, with other pharmaceutically active compounds.

Dosage levels of the order of from about 0.01 mg to about 140 mg/kg of body weight per day are useful in representative embodiments, or alternatively about 0.5 mg to about 7 g per patient per day. Those of skill will readily appreciate that dose levels can vary as a function of the specific compound, the severity of the symptoms and the susceptibility of the subject to side effects. Dosages for a given compound are readily determinable by those of skill in the art by a variety of means.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, such as 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular peptidomimetic compound employed and the effect to be achieved, and the pharmacodynamics associated with each compound in the host. Those of skill in the art will readily appreciate that dose levels can vary as a function of the specific compound, the nature of the delivery vehicle, and the like. Preferred dosages for a given compound or agent are readily determinable by those of skill in the art by a variety of means.

Kits & Systems

Also provided are kits and systems that find use in practicing embodiments of the methods, such as those described as described above. The term "system" as employed herein refers to a collection of two or more different active agents, present in a single or disparate composition, that are brought together for the purpose of practicing the subject methods. The term kit refers to a packaged active agent or agents. In some embodiments, the subject system or kit includes a dose of a subject naphthalene derivative compound (e.g., as described herein) and a dose of a second active agent (e.g., as described herein) in amounts effective to treat a subject for a target disease or condition.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

Examples

I. Introduction

In this study we screened and assessed FDA approved drugs for PAM activity in vitro at the α7 nAChR. We also created structurally novel derivatives of one of the drugs, propranolol.

II. Methods

A. Pharmacophore Modeling

A common feature pharmacophore was developed based on galantamine using commercially available software (Discovery Studio vers 4.1, Biovia, San Diego, Calif.), as described in detail in Ekins et al., "alpha7-Nicotinic acetylcholine receptor inhibition by indinavir: implications for cognitive dysfunction in treated HIV disease," AIDS (May 15, 2017) 31: 1083-1089. Briefly, we started by using galantamine as the template of a common feature pharmacophore model and this was then used to search a 3D database of FDA approved drugs and commercially available compounds. (Motel et al., "Cholinergic modulation by opioid receptor ligands: potential application to Alzheimer's disease," Mini Rev Med Chem (2013) 13: 456-466.

B. In Vitro Patch-Clamp Assay for PAM Activity at the α7 nAChR

The in vitro patch-clamp assay for PAM activity at the α7 nAChR was performed with PNU-120596 as a positive control. All patch-clamp testing was performed by an independent contract research company, ChanTest (Charles River) in the USA. For patch-clamp measurements, recordings of currents through α7 nAChR were made in a blinded fashion. Measurements of concentration-response and rate-dependence of test articles on α7 nAChR activation kinetics were performed with data collected. The significance of test article effects were evaluated versus parallel vehicle and positive control (PNU-120596) recordings. For all of the compounds, a dose response curve over the range of concentrations tested was then generated.

Test article effects were evaluated in 8-point concentration-response format (4 replicate wells/concentration). All test and control solutions contained 0.3% DMSO. The test article formulations were loaded in a 384-well compound plate using an automated liquid handling system (SciClone ALH3000, Caliper LifeScienses). To verify the sensitivity of the assay, the standard agonist positive control article—PNU-120596 (PAM) was applied at 8 concentrations, 4 replicates per concentration.

CHO cells (ATCC, Manassas, Va.) were maintained in tissue culture incubators per ChanTest SOP. Stocks were maintained in cryogenic storage. Cells used for electrophysiology were plated in 150-mm plastic culture dishes. CHO cells were transfected with the appropriate ion channel or receptor cDNA(s). Cells were cultured in Ham's F-12 supplemented with 10% fetal bovine serum, 100 U/mL penicillin G sodium, 100 μg/mL streptomycin sulfate, and the appropriate selection antibiotics.

The effects were evaluated using IonWorks™ Barracuda system (MDC) using the following electrophysiological procedures: Intracellular solution (mM) consisted off 90 CsF, 50 CsCl, 2 $MgCl_2$, 5 EGTA 10 HEPES, adjusted to pH 7.2 with CsOH. In preparation for a recording session, the intracellular solution was loaded into the intracellular compartment of the PPC planar electrode. Extracellular solution, HB-PS (composition in mM) consisted of 137 NaCl, 4 KCl, 1.8 $CaCl_2$, 1 $MgCl_2$, 10 HEPES, 10 glucose; pH 7.4 adjusted with NaOH. The holding potential was −70 mV. Extracellular buffer was loaded into the PPC plate wells (11 uL per well). Cell suspension was pipetted into the wells (9 uL per well) of the PPC planar electrode. Whole-cell recording configuration was established via patch perforation with membrane currents recorded by on-board patch clamp amplifiers. One recording was performed during application of test articles to detect agonist effects or during co-application of test articles with 1 mM acetylcholine to detect modulation effects. The application consisted of the addition of 20 μL of 1× concentrated test article solution and agonist at 20 uL/s (1 second total application time).

PAM effect of test articles on the channel was calculated as: % activation=$(I_{TA}/I_{AC}) \times 100\%$, where $I_{TA}$ was the current elicited with 1000 uM Acetylcholine in the presents of $I_{TA}$ and $I_{AC}$ was the averaged current elicited with the 1000 uM Acetylcholine with 0.3% DMSO C. Design of Structurally Novel Propranolol Derivatives The 3-D structure for the α7-nAChR has not yet been determined, consequently we used acetylcholine binding protein as a substitute for the computer based binding affinity simulations. The 3-D structure of acetylcholine binding protein was downloaded from the National Protein Data Bank (www.rcsb.org) and the 3-D structure for propranolol was downloaded from DrugBank.ca.gov. An exhaustive set of potential derivatives was then created by systematically replacing single hydrogen atoms in propranolol with either a methyl, hydroxyl, or carbonyl group at all possible locations along the carbon chain of the molecule using the commercially available program Visual Molecular Dynamics (VMD, available at http://www.ks.uiuc.edu/Research/vmd/). A second commercially available program, PyRx (available at http://pyrx.sourceforge.net/), was then used to determine the predicted binding affinities between individual derivatives and the α7-nAChR.

D. Synthesis of Structurally Novel Propranolol Derivatives

Synthesis of structurally novel propranolol derivatives was performed by a contract research company (BioFocus, Inc., United Kingdom). The structures for all compounds synthesized were confirmed through three methods: high-performance liquid chromatography (HPLC), mass spectroscopy (MS), and nuclear magnetic resonance (NMR) studies.

III. Results

A. Virtual Screen

The pharmacophore based on galantamine consisted of two hydrophobic features, a hydrogen bond acceptor, a hydrogen bond donor, and a positive ionizabile feature. After screening over 1000 molecules, over 160 remaining molecules that mapped to the pharmacophore were filtered to identify potentially repurposable α7-nAChR PAMs. Molecules that mapped well to the features of either pharmacophore were identified and known PAMs or problematic compounds were removed. The selected compounds (Table 1) were then tested in vitro.

TABLE 1

$EC_{50}$ ($IC_{50}$) values of Test Articles

| TA # | TA ID | $EC_{50}$ ($IC_{50}$), μM Peak | 0.5-AUC |
|---|---|---|---|
| 1 | Carvedilol | (18.9) | (4.4) |
| 2 | Alfuzosin hydrochloride | (22.9) | (14.2) |

TABLE 1-continued $EC_{50}$ ($IC_{50}$) values of Test Articles

| TA # | TA ID | $EC_{50}$ ($IC_{50}$), μM Peak | 0.5-AUC |
|---|---|---|---|
| 3 | Riboflavin | ND | ND |
| 4 | Bromocriptine | ND | (66.1) |
| 5 | Propanolol | (15.9) | (5.3) |
| 6 | Fexofenadine | ND | ND |
| 7 | O-Desmethyl Galantamine | ND | ND |
| 8 | N-Desmethyl Galantamine | ND | ND |
| 9 | Galantamine hydrobromide | ND | ND |
| PC | PNU-120596 | 1.066 | 1.215 |

B. Patch Clamp Studies of FDA Approved Compounds and Galantamine Derivatives

Three compounds, riboflavin, bromocriptine, and propranolol, were identified as displaying PAM effects at the α7-nAChR (FIG. 1) in addition to galantamine and two galantamine derivatives that displayed measurable α7-nAChR PAM activity at lower concentrations (see FIG. 1). Furthermore, three compounds, carvedilol, alfuzosin hydrochloride, and propranolol, were identified as showing inhibitor effects at the α7-nAChR (See Table 1, above). The IC50 value was greatest for alfuzosin (IC50=22.9), followed by carvedilol (IC50=18.9), and was lowest for propranolol (IC50-15.9).

Figure 2:
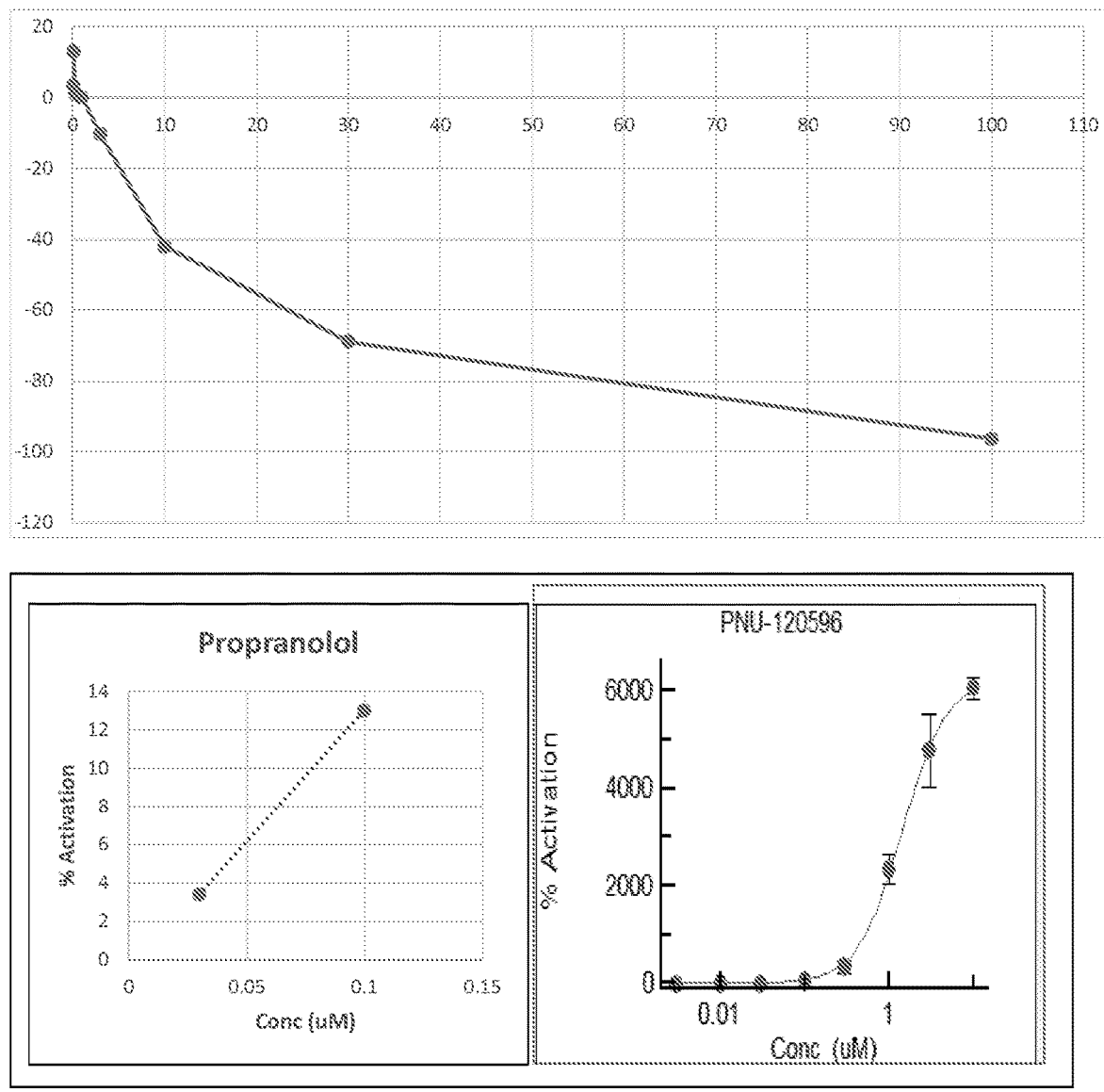
FIG. 2: Comparison of α7-nAChR patch-clamp results for Propranolol and PNU-120596.

Not only did propranolol yield a magnitude of the PAM effect on α7-nAChR that was much lower than that of the commercially available PAM compound that was used as a positive control PNU-120596, (see FIG. 2), but it also displayed evidence of functional inhibition at higher concentrations (see FIG. 2). Functional inhibition is not seen with most other commercial α7-nAChR compounds, including PNU-120596 which does not display any evidence of functional inhibition (see FIG. 2)

C. Binding Affinity Studies of Propranolol Modifications

Figure 3:
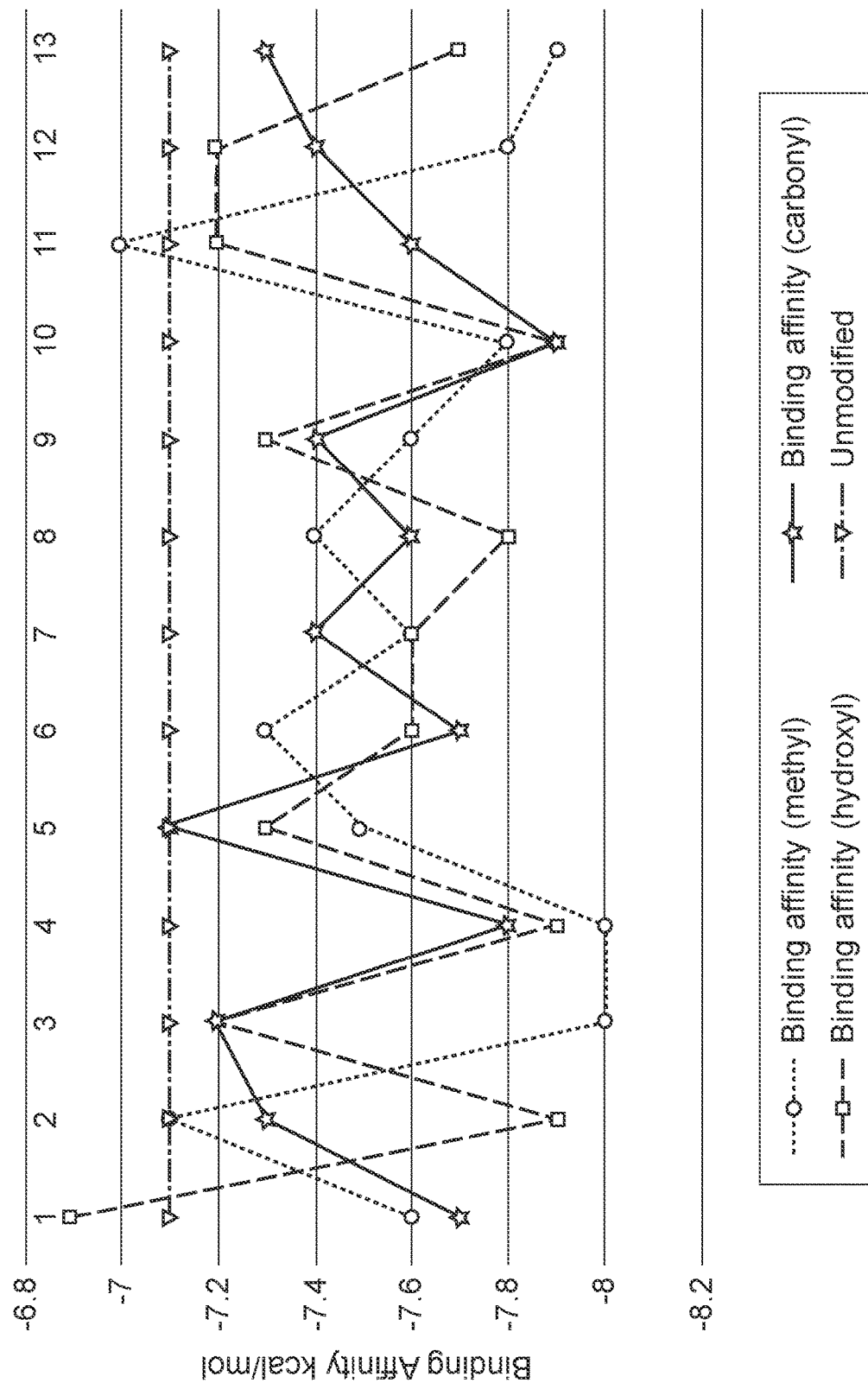
FIG. 3: Binding Affinity vs. Location of Propranolol Derivatives.

Binding affinity calculations for all possible propranolol modifications consisting of addition of either methyl, hydroxyl, or carboxyl groups along the carbon chain of the molecule were calculated using PyRx and graphed relative to the position of the modification in the molecule (See FIG. 3). While multiple types and locations of modifications were able to increase the binding affinity with the α7-nAChR, we selected 4 structures to synthesize, including one structure (derivative 6) for which two stereoisomers were possible. For derivative 6 we decided to have both enantiomers (R and S) synthesized and tested. The structures are summarized in Table 2.

TABLE 2

Chemical Formula and Molecular Weight of the Propranolol Derivatives

| Compound | Formula | Weight |
|---|---|---|
| BF000825289 (V2) | C16H21NO3 | 275.34 |
| BF000825198 (V4) | C17H23NO2 | 273.37 |
| BF000825197 (V5) | C17H23NO2 | 273.37 |
| BF000825199 (V6_R) | C17H23NO2 | 273.37 |
| BF000825200 (V6_S) | C17H23NO2 | 273.37 |

The structures are shown below:

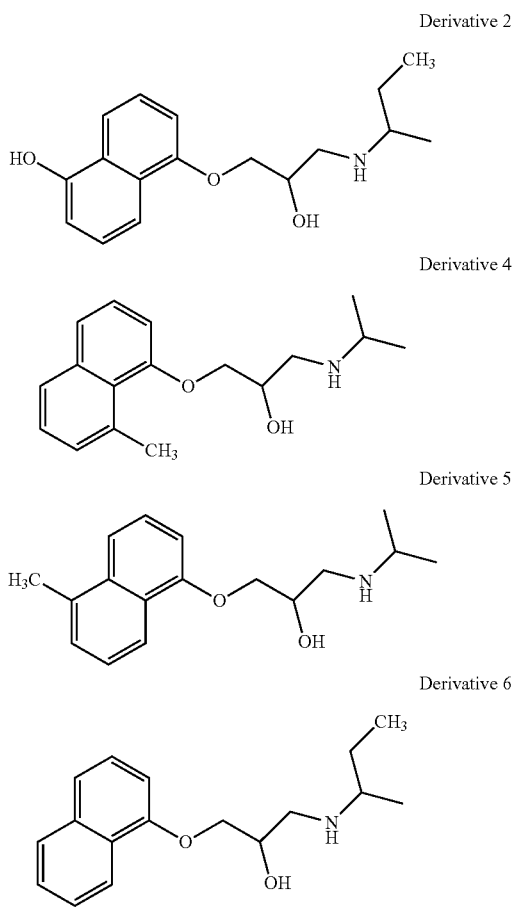

D. Patch clamp studies of Structurally Novel Propranolol Derivatives

Figure 4:
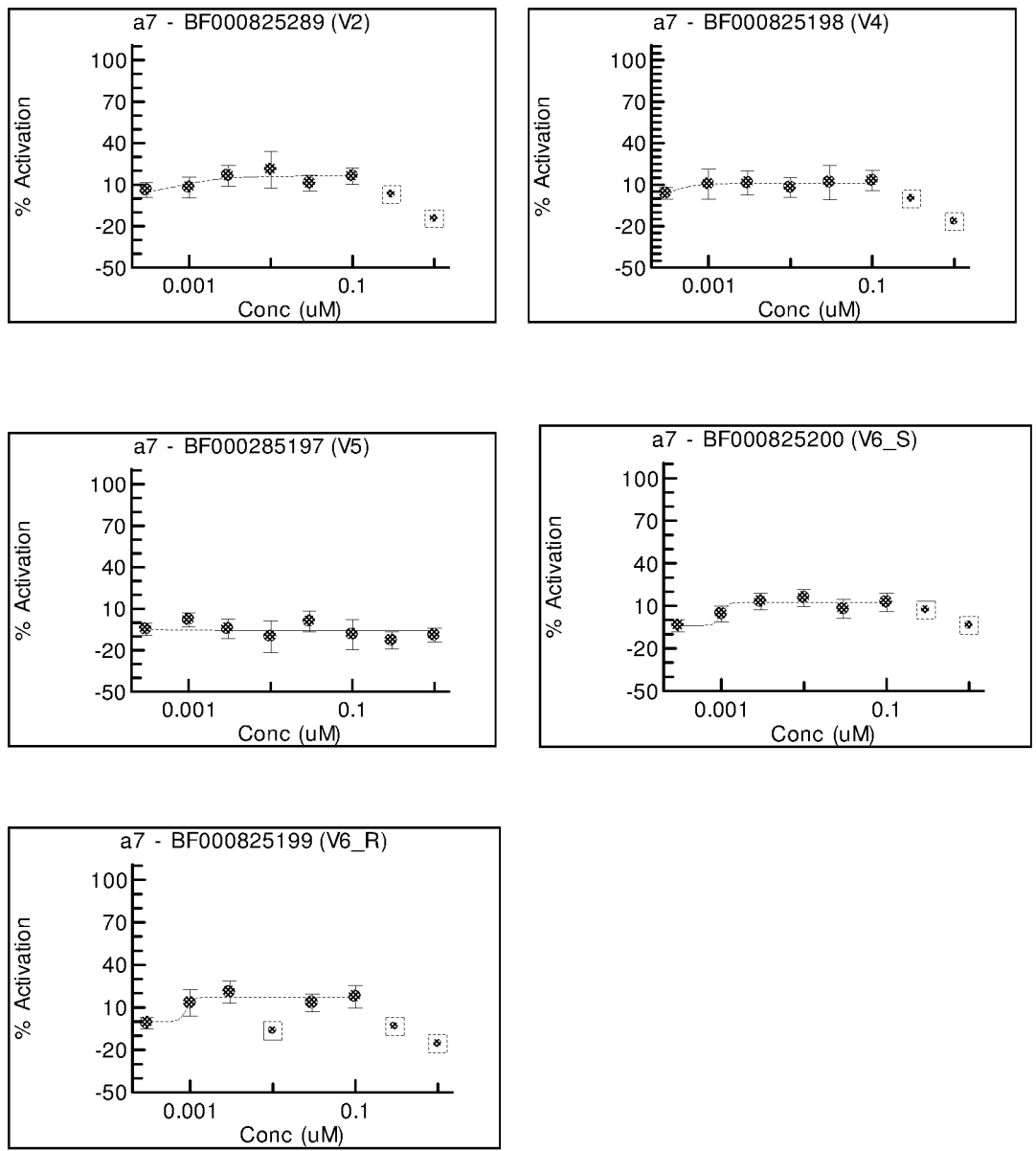
FIG. 4: Patch-clamp Studies of Structurally Novel Propranolol Derivatives A. V2, B V4, C V5, D V6S, E V6R.

Of the five structurally novel propranolol derivatives tested, four (Derivative 2, 4, 6S, and 6R) displayed PAM effects at the α7-nAChR (See FIG. 4). All of the structurally novel propranolol derivatives that displayed α7 nAChR PAM activity not only had milder magnitudes of effect than PNU-120596 (similar to the magnitude of effect displayed by propranolol and galantamine), but these compounds also all displayed a more physiologically normal effect at the α7 nAChR that included functional inhibition at higher concentrations (See FIG. 4).

IV. Discussion

Current therapies for Alzheimer's disease are less than optimal as they are purely symptomatic with no disease modifying effect. To date there are no medications available that target the underlying histopathological changes associated with the disease: formation of β-amyloid and tau protein aggregates. The α7-nAChR agonists comprise one class of compounds that are potentially disease modifying through disruption of the interaction between β-amyloid and α7-nAChR. Consequently, developing novel compounds that act through this mechanism and are well tolerated is an active area of research for creating potential new therapeutic agents in AD. In this study, we identified commercially available compounds with previously unknown α7-nAChR PAM functionality. For one compound, propranolol, we created four structurally novel derivatives that displayed α7-nAChR PAM functionality as well as functional inhibition. Further testing of propranolol—as well as all compounds with α7-nAChR PAM functionality—in vivo for possible development as new therapeutic agents for the treatment of AD is likely warranted based on these preliminary studies.

Propranolol is particularly well suited for potential repurposing as an α7-nAChR PAM, as it is already FDA approved for treatment of a variety of medical disorders in the United States (high blood pressure, irregular heartbeat, essential tremors, anxiety, etc.) and has a long history of use in many countries. In general, propranolol is considered to be a safe medication that requires no blood-test monitoring, has minimal side effects, typically doses well below toxic levels, and is usually well tolerated. The medication is well known to act as a non-selective β-blocker without sympathomimetic activity. It also has membrane stabilizing activity, and is highly lipid soluble which-when coupled with its small molecular weight-allows for good blood brain barrier penetration. We feel this medication is ideal for repurposing and, consequently, further testing in patients suffering from Alzheimer's disease is urgently needed.

The usefulness of a well-tolerated and effective α7-nAChR PAM compound will extend beyond treatment of Alzheimer's disease. For instance, β-amyloid and tau protein deposition have been implicated in the pathogenesis of several other neurodegenerative disorders which, therefore, may also be amenable to treatment with α7-nAChR agonist compounds. Relatively common and currently untreatable disorders-schizophrenia and dementia in Parkinson's disease in particular—are targets for treatment with α7-nAChR PAMs. (Wang et al., "β-amyloid (1-42) binds to alpha7 nicotinic acetylcholine receptor with high affinity. Implications for Alzheimer's disease pathology," J Biol Chem (2000) 275: 5626-5632). The compounds described herein may be used for treatment of such diseases.

Several α7-nAChR PAM compounds have been developed by various pharmaceutical companies and have gone on to clinical trials, including: A-582941 (2-methyl-5-(6-phenyl-pyridazin-3-yl)-octahydro-pyrrolo[3,4-c]pyrrole; Abbott Laboratories), ABT-107 (5-(6-[(3R)-1-azabicyclo[2,2,2]oct-3-yloxy]pyridazin-3-yl)-1H-indole; Abbott Laboratories), EVP-6124 (Elan Pharmaceuticals, Dublin, Ireland), SB-206553 (3,5-dihydro-5-methyl-N-3-pyridinylbenzo[1,2-b:4,5-b0]-dipyr-role-1 (2H)-carboxamide), PNU-120596 (1-(5-chloro-2,4-dimethoxy-phenyl)-3-(5-methyl-isoxazol-3-yl)-urea; GSK Pharmaceuticals), Encenicline (R)-7-chloro-N-quinuclidin-3-yl)benzo[b]thiophene-2-carboxamide; Forum Pharmaceuticals).

These compounds, which possessed in vitro activity similar in magnitude to PNU-120596 without functional inhibition, have been tried in various Phase 1-3 clinical trials but none have been able to demonstrate a clear disease modifying effect. Additionally, in September 2015 the FDA placed a clinical hold on three Phase 3 studies of an α7-nAChR PAM in Alzheimer's disease (still in place and further clinical research with these compounds is currently prohibited) and one Phase 1 study in schizophrenia (later partially lifted). Anon (2015) Encenicline. The clinical hold was specific to the compound being studied (Encenicline) and its severe gastrointestinal side effect that occurs due to overstimulation of nicotinic receptors. Anon (2015) Encenicline. The other clinical trials of α7-nAChR PAM compounds have all failed due to lack of efficacy and are no longer being developed as potential new drugs.

The failure of α7-nAChR PAM compounds in clinical trials due either to an inability to demonstrate meaningful clinical benefit or to serious adverse events has been a large set back in the field, delaying the introduction of this class of potential therapeutic compounds to the market. These failures have been attributed in part to excessive overstimulation of the α7-nAChR which then causes neuronal excitotoxicity (Guerra-Alvarez et al., "Positive allosteric modulation of alpha-7 nicotinic receptors promotes cell death by inducing Ca(2+) release from the endoplasmic reticulum," J Neurochem (2015) 133: 309-319). In general, the α7-nAChR PAM compounds that have been tested in clinical trials—and have failed—demonstrated a current across the receptor in in vitro studies that was augmented by as much as 6,000% of normal (Id.). From compounds with similar activity profiles, such stimulation of neuronal nAChRs has been shown to induce neuronal cell death through excitotoxicity(Id.). Consequently, an α7-nAChR PAM compound with a more modest effect, such as that demonstrated by propranolol, offers a therapeutic alternative that finally realizes the potential benefits of α7-nAChR PAM compounds in AD without causing adverse events related to overstimulation of the α7-nAChR.

V. Conclusion

In this study we have identified previously unknown α7 nAChR PAM activity in vitro for several FDA approved medications, including propranolol. When compared to other α7 nAChR PAM compounds that have failed in clinical trials, propranolol possesses a milder and more physiologically normal augmentation of current across the α7 nAChR. The milder α7 nAChR PAM effect of propranolol allows for it to exhibit the positive and beneficial aspects related to disruption of interactions between the α7 nAChR and β-amyloid protein without resulting in adverse events related to excessive overstimulation of the α7 nAChR. We also designed structurally novel propranolol derivatives with α7 nAChR PAM activity.

Notwithstanding the appended clauses, the disclosure is also defined by the following clauses:
1. A method of modulating the interaction between β-amyloid and α7-nAChR in a cell, the method comprising:
  contacting the cell with a naphthalene derivative to modulate the interaction between β-amyloid and α7-nAChR in the cell.
2. The method according to Clause 1, wherein naphthalene derivative has the structure of formula (I):

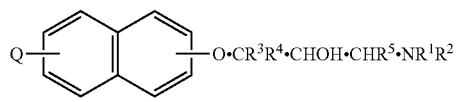

wherein:
  $R^1$ is H or alkyl, cycloalkyl, alkenyl, aralkyl or alkanoyl radical, any of which may optionally be substituted;
  $R^2$ is H or alkyl, cycloalkyl, alkenyl, alkynyl, or aralalkyl radical, any of which may optionally be substituted;
  wherein R1 and R2 may joined together with the nitrogen atom to form a heterocyclic radical, which may optionally be substituted;
  $R^3$, $R^4$, and $R^5$ are independently H or alkyl, which may optionally be substituted; and Q is optional and, if present, may be halogen, alkyl, substituted alkyl, hydroxy, alkoxy, substituted alkoxy, cyano, nitro, carboxy, carboxyamide, substituted carboxyamide, —$SO_3H$, sulfonamide, substituted sulfonamide, aryl, substituted aryl, heteroaryl, substituted heteroaryl, heterocycle and substituted heterocycle.
3. The method according to Clause 2, wherein the naphthalene derivative is propranolol.
4. The method according to Clause 2, wherein the naphthalene derivative has the structure selected from the group consisting of:

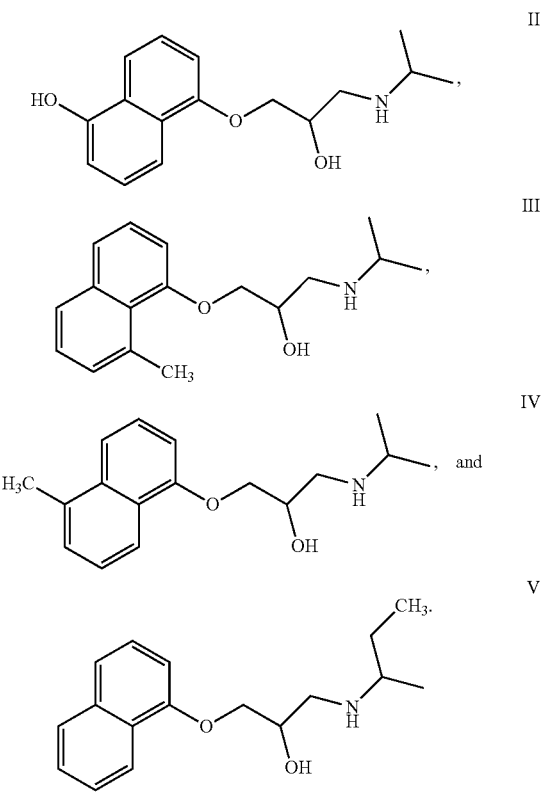

5. The method according to any of the preceding clauses, wherein the cell is in vitro.
6. The method according to any of the preceding clauses, wherein the cell is in vivo.
7. A method of treating a subject for a neurodegenerative disease, the method comprising:
  administering to a subject an effective amount of a naphthalene derivative to treat the subject for the neurodegenerative disease.
8. The method according to Clause 7, wherein naphthalene derivative has the structure of formula (I):

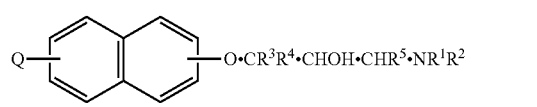

wherein:
  $R^1$ is H or alkyl, cycloalkyl, alkenyl, aralkyl or alkanoyl radical, any of which may optionally be substituted;

R[2] is H or alkyl, cycloalkyl, alkenyl, alkynyl, or aralalkyl radical, any of which may optionally be substituted;

wherein R1 and R2 may joined together with the nitrogen atom to form a heterocyclic radical, which may optionally be substituted;

R[3], R[4], and R[5] are independently H or alkyl, which may optionally be substituted; and Q is optional and, if present, may be halogen, alkyl, substituted alkyl, hydroxy, alkoxy, substituted alkoxy, cyano, nitro, carboxy, carboxyamide, substituted carboxyamide, —SO₃H, sulfonamide, substituted sulfonamide, aryl, substituted aryl, heteroaryl, substituted heteroaryl, heterocycle and substituted heterocycle.

9. The method according to Clause 8, wherein the naphthalene derivative is propranolol.

10. The method according to Clause 8, wherein the naphthalene derivative has the structure selected from the group consisting of:

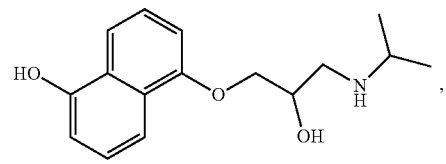

II

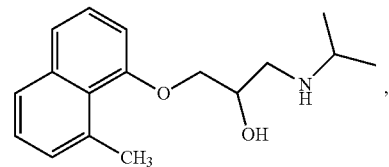

III

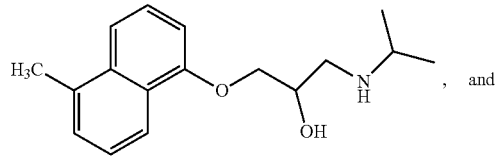

, and

IV

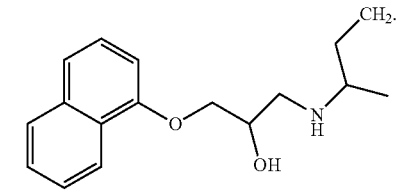

V

11. The method according to any of Clause 7 to 10, wherein the neurodegenerative disease is selected from the group consisting of: Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy and dementia.

12. The method according to Clause 11, wherein the neurodegenerative disease is Alzheimer's disease.

13. The method according to any of Clauses 7 to 12, wherein the subject is a mammal.

14. The method according to Clause 13, wherein the subject is a human.

15. A pharmaceutical composition comprising:
a) a naphthalene derivative selected from the group consisting of:

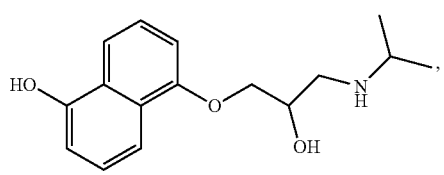

II

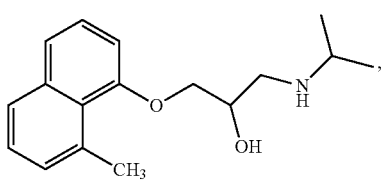

III

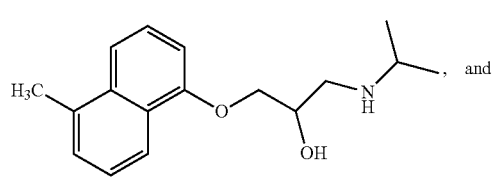

, and

IV

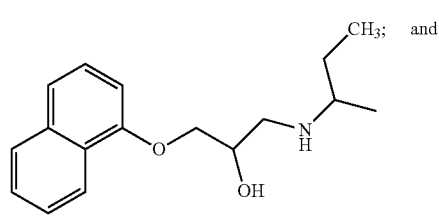

; and

V

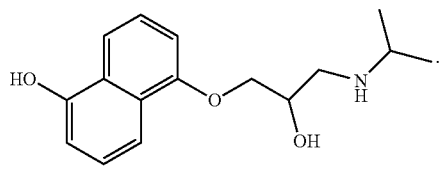

b) a pharmaceutical delivery vehicle.

16. The pharmaceutical composition according to Clause 15, wherein the naphthalene derivative has the structure of formula (II):

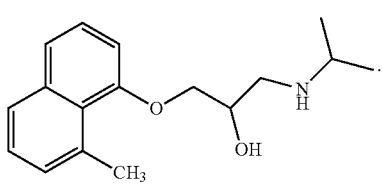

II

17. The pharmaceutical composition according to Clause 15, wherein the naphthalene derivative has the structure of formula III:

III

18. The pharmaceutical composition according to Clause 15, wherein the naphthalene derivative has the structure of formula (IV):

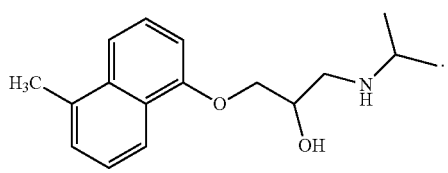

IV

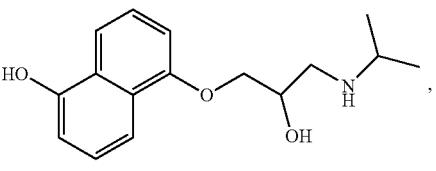

II

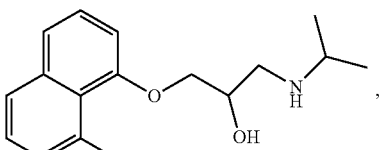

III

19. The pharmaceutical composition according to Clause 15, wherein the naphthalene derivative has the structure of formula (V):

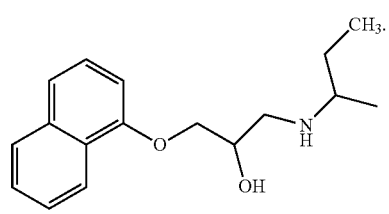

V

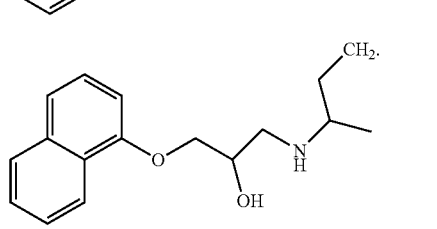

IV, and

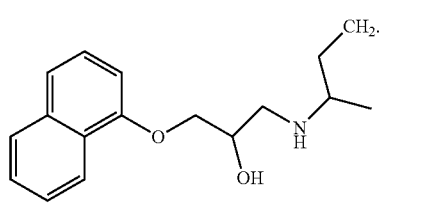

V

20. A kit comprising:
  a dose of a naphthalene derivative compound; and
  a dose of a second active agent having neurodegenerative disease therapeutic activity.

21. The kit according to Clause 20, wherein the naphthalene derivative has the structure of formula (I):

formula (I):

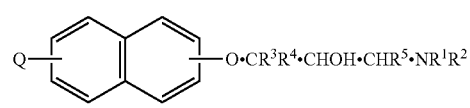

(I)

wherein:

$R^1$ is H or alkyl, cycloalkyl, alkenyl, aralkyl or alkanoyl radical, any of which may optionally be substituted;

$R^2$ is H or alkyl, cycloalkyl, alkenyl, alkynyl, or aralalkyl radical, any of which may optionally be substituted;

wherein R1 and R2 may joined together with the nitrogen atom to form a heterocyclic radical, which may optionally be substituted;

$R^3$, $R^4$, and $R^5$ are independently H or alkyl, which may optionally be substituted; and Q is optional and, if present, may be halogen, alkyl, substituted alkyl, hydroxy, alkoxy, substituted alkoxy, cyano, nitro, carboxy, carboxyamide, substituted carboxyamide, —SO$_3$H, sulfonamide, substituted sulfonamide, aryl, substituted aryl, heteroaryl, substituted heteroaryl, heterocycle and substituted heterocycle.

22. The kit according to Clause 20, wherein the naphthalene derivative is propranolol.

23. The kit according to Clause 20, wherein a naphthalene derivative is selected from the group consisting of:

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject for a neurodegenerative disease, the method comprising:
  administering to the subject an effective amount of a compound selected from the group consisting of:

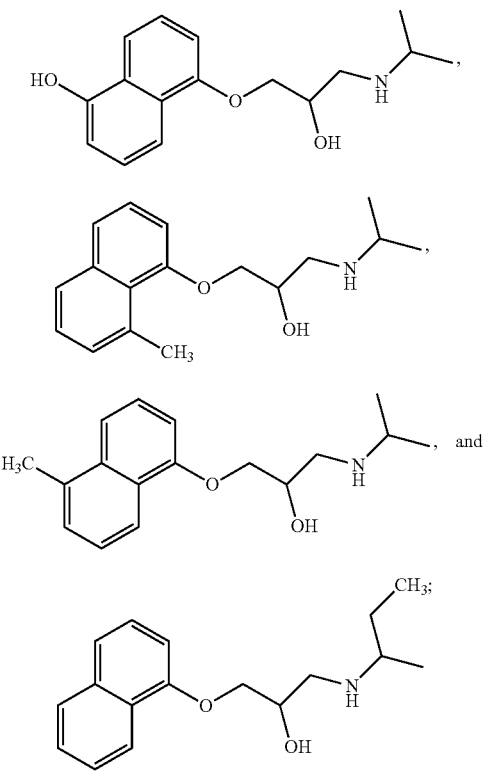

to treat the subject for the neurodegenerative disease.

2. The method according to claim 1, wherein the neurodegenerative disease is selected from the group consisting of: Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy and dementia.

3. The method according to claim 2, wherein the neurodegenerative disease is Alzheimer's disease.

4. The method according to claim 1, wherein the subject is a mammal.

5. The method according to claim 4, wherein the subject is a human.

6. A pharmaceutical composition comprising:
a) a compound selected from the group consisting of:

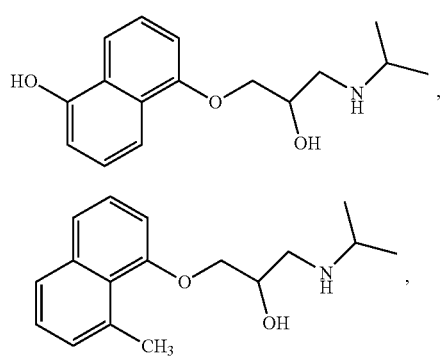

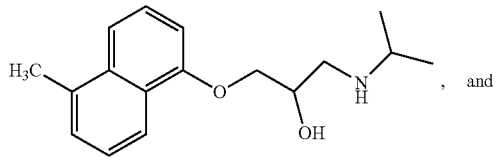

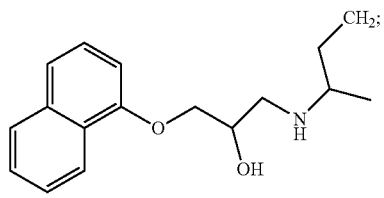

and
b) a pharmaceutical delivery vehicle.

7. A kit comprising:
a dose of a compound selected from the group consisting of:

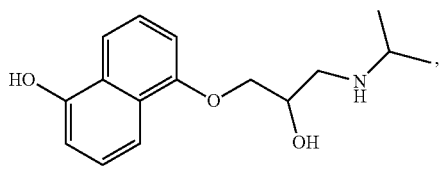

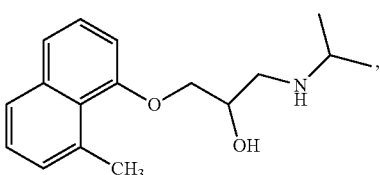

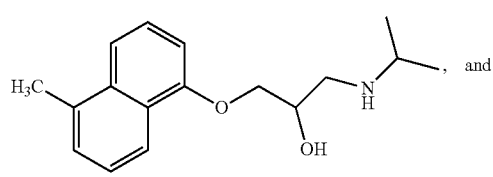

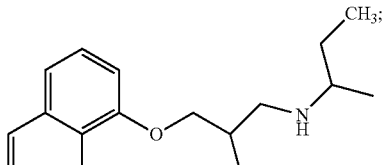

and
a dose of a second active agent having neurodegenerative disease therapeutic activity.

* * * * *

UNITED STATES PATENT AND TRADEMARK OFFICE
CERTIFICATE OF CORRECTION

PATENT NO. : 11,382,875 B2
APPLICATION NO. : 16/498898
DATED : July 12, 2022
INVENTOR(S) : McMurtray et al.

It is certified that error appears in the above-identified patent and that said Letters Patent is hereby corrected as shown below:

In the Specification

Please replace "pyrmidine" with -- pyrimidine -- (Column 7, Line 15);
Please replace "C(NR$^{70}$)R" with -- C(NR$^{70}$)R$^{70}$ -- (Column 7, Line 50);
Please replace "C(O)NR$^{80}$R$^{88}$" with -- C(O)NR$^{80}$R$^{80}$ -- (Column 8, Line 24);
Please replace "NR$^{70}$C(O)R$^{80}$" with -- NR$^{70}$C(O)R$^{70}$ -- (Column 8, Line 26);
Please replace "CH$_2$" in the chemical structure with -- CH$_3$ -- (Column 35, Line 43); and
Please replace "CH$_2$" in the chemical structure with -- CH$_3$ -- (Column 38, Line 24).

In the Claims

Please replace "CH$_2$" in the chemical structure with -- CH$_3$ -- in Claim 6 (Column 40, Line 11).

Signed and Sealed this
Twenty-seventh Day of September, 2022

Katherine Kelly Vidal
*Director of the United States Patent and Trademark Office*